(12) United States Patent
Owen

(10) Patent No.: US 6,331,704 B1
(45) Date of Patent: Dec. 18, 2001

(54) HYDRAULIC FLUID CONTAMINATION MONITOR

(75) Inventor: Allan B. Owen, Exton, PA (US)

(73) Assignee: Vickers, Incorporated, Maumee, OH (US)

(*) Notice: Subject to any disclaimer, the term of this patent is extended or adjusted under 35 U.S.C. 154(b) by 0 days.

(21) Appl. No.: 09/193,067

(22) Filed: Nov. 16, 1998

Related U.S. Application Data (60) Provisional application No. 60/072,985, filed on Jan. 20, 1998.

(51) Int. Cl.[7] .................................................. G01N 33/26
(52) U.S. Cl. ................................ 250/339.11; 250/227.22
(58) Field of Search .................... 250/339.11, 227.22, 250/574; 356/336, 338

(56) References Cited

U.S. PATENT DOCUMENTS

| | | | |
|---|---|---|---|
| 3,588,890 | 6/1971 | Cox et al. | 340/409 |
| 3,646,552 | 2/1972 | Fuhr | 340/409 |
| 4,070,660 | 1/1978 | Tauber | 340/236 |
| 4,127,808 | 11/1978 | Sproul et al. | 324/65 R |
| 4,160,914 * | 7/1979 | Wynn | 250/574 |
| 4,178,103 | 12/1979 | Wallace . | |
| 4,236,146 | 11/1980 | Clark et al. | 340/517 |
| 4,306,525 | 12/1981 | Faxvog . | |
| 4,467,637 | 8/1984 | Rumberger | 73/61 |
| 4,598,280 | 7/1986 | Bradford | 340/631 |
| 4,668,944 | 5/1987 | Teass, Jr. | 340/603 |
| 4,673,912 | 6/1987 | Kumasaka et al. | 340/52 R |
| 4,850,707 | 7/1989 | Bowen et al. . | |
| 5,007,733 | 4/1991 | Laurent et al. . | |
| 5,045,840 | 9/1991 | Berrier et al. | 340/652 |
| 5,166,880 | 11/1992 | Furui | 364/424.05 |
| 5,187,465 | 2/1993 | Stonerook et al. | 340/438 |
| 5,250,909 | 10/1993 | Bitts | 324/542 |
| 5,262,841 * | 11/1993 | Blesener et al. | 356/338 |
| 5,406,208 | 4/1995 | Bitts | 324/537 |
| 5,438,420 | 8/1995 | Harwick et al. | 356/440 |
| 5,459,569 * | 10/1995 | Knollenberg et al. | 356/338 |
| 5,509,375 * | 4/1996 | Sayka et al. | 118/712 |
| 5,583,441 | 12/1996 | Bitts | 324/553 |
| 5,742,234 | 4/1998 | Owen | 340/631 |
| 6,097,025 * | 8/2000 | Modlin et al. | 250/227.22 |

* cited by examiner

Primary Examiner—Constantine Hannaher
Assistant Examiner—Otilia Gabor
(74) Attorney, Agent, or Firm—Emch, Schaffer, Schaub & Porcello, Co., L.P.A.

(57) ABSTRACT

The presence of particulate debris flowing in a hydraulic fluid flow system includes a source of infra-red light passing through a window of the fluid flow line while fluid is flowing therethrough. A portion of the light is directed to a monitoring photodiode prior to reaching the fluid flow line. A detector photodiode is positioned to receive light passing through the flow line, the hydraulic fluid flowing therethrough and out of a second window. A trap is positioned between the hydraulic fluid flow line and the detector photodiode to prevent the direct rays of light from reaching the detector photodiode while permitting scattered light to reach the detector photodiode. A reduction in the amount of light reaching the detector photodiode results in an alarm being activated.

31 Claims, 6 Drawing Sheets

HYDRAULIC FLUID CONTAMINATION MONITOR

CROSS REFERENCE TO RELATED APPLICATION

This application is based on Provisional Patent Application Serial No. 60/072,985 filed Jan. 20, 1998.

The present invention is directed to a method and apparatus for detecting suspension of particulate debris in hydraulic fluid systems. More specifically, the invention is directed to a device and method for both detecting the presence of such particles and monitoring an increase in the quantity or density of such particles while the hydraulic fluid is flowing through a hydraulic or other fluid flow line. The invention is particularly useful in that it can be mounted directly on a vehicle, industrial equipment including mobile equipment or specialized power machinery.

Under the present invention, a fluid specification monitor (FSM) is mounted to optically view and monitor the hydraulic fluid as it flows through a fluid flow line of the hydraulic system for example, in the hydraulic return line. The monitor can physically fit into the hydraulic fluid flow line. Under one embodiment, the portion of the fluid flow line being monitored can have the same flow area as the adjacent portions of the fluid flow line so that it will not create an added pressure drop to the system.

In one embodiment, a light emitting diode directs a beam of light through an aperture and then through a beam splitter, so that a sample of the axial light source can be taken by a monitoring photodiode to ascertain the amount of light being emitted by the diode source. The rest of the light is directed along the axial path through the liquid which is flowing as a small column through the fluid flow line. The fluid flow line is provided with windows of glass or a synthetic sapphire material which permit the light beam to pass through the fluid flow line and the hydraulic fluid flowing therethrough. On the opposite side of the fluid flow line is at least one collection lens. A light trap or mask is provided along an axis defined by the light emitting diode and the center of the collection lens in order to block any in-line light directly from the source. The light trap or mask is confined to the central portion of the collection lens lying within a small radius of the in-line axis so that scattered light radially outwardly of the mask will pass through the lens or lenses and will direct the light to a photodiode and amplifier electrically connected thereto. Particles, water and air bubbles, and other contaminants in the fluid will reflect and scatter part of the in-line light beam and this scattered light is to be detected optically. If the contamination level in the hydraulic fluid increases beyond a predetermined level, the photodiode will cause the electrical signal emitted by the amplifier to increase. Upon an increase beyond a predetermined amount, the monitor will set off an alarm to thereby permit the operator to take corrective action before the system is damaged.

The monitoring system of the present invention is not intended to detect or count individual particles but rather indicates the relative amount of light scattered from an aggregate amount of material moving through the oil chamber, as the light passes through the hydraulic fluid flowing through such oil chamber (i.e., a section of the fluid flow line). It is preferred that the monitoring system have digital electronics rather than analog electronics as a digital monitoring system is better able to process the optical signal and to compensate for variations in temperature of the infra-red light emitting diode and photodiode. Although analog circuitry is difficult to compensate for such variations in temperature, it is suitable for many applications.

REFERRING TO THE DRAWINGS

DETAILED DESCRIPTION

Figure 1:
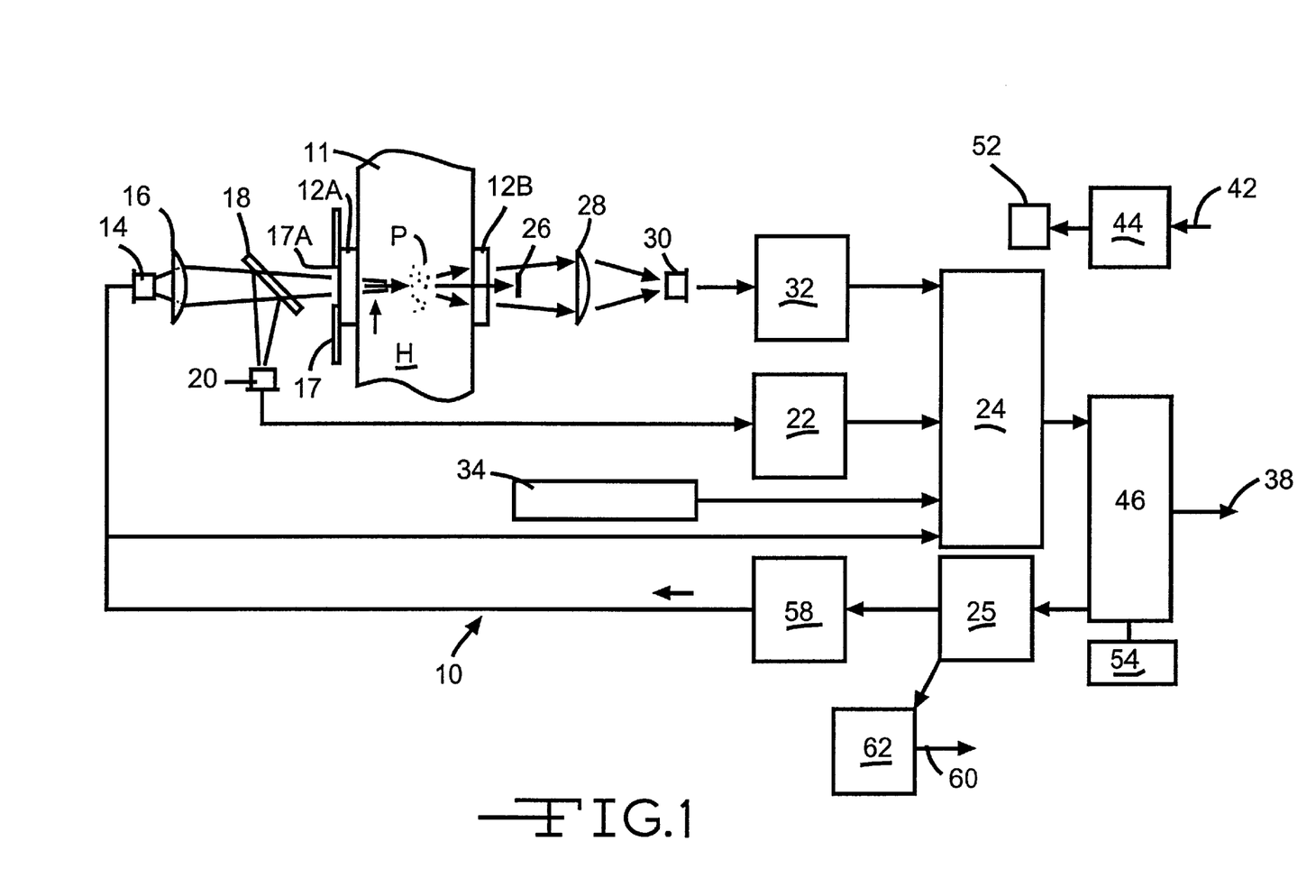
FIG. 1 is an opto-electronic block diagram for the monitor of the present invention.
Figure 2:
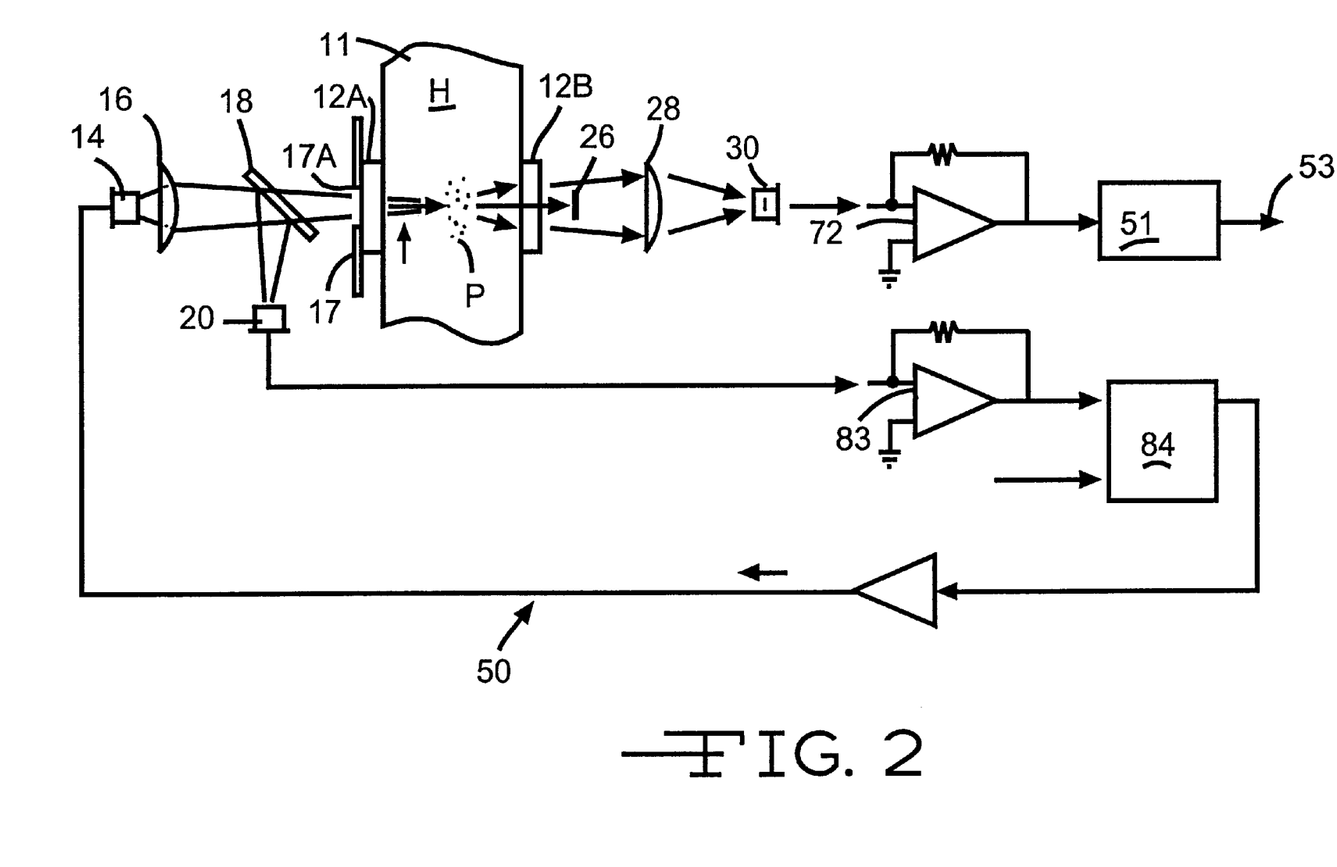
FIG. 2 is an opto-electronic block diagram of another embodiment.
Figure 3:
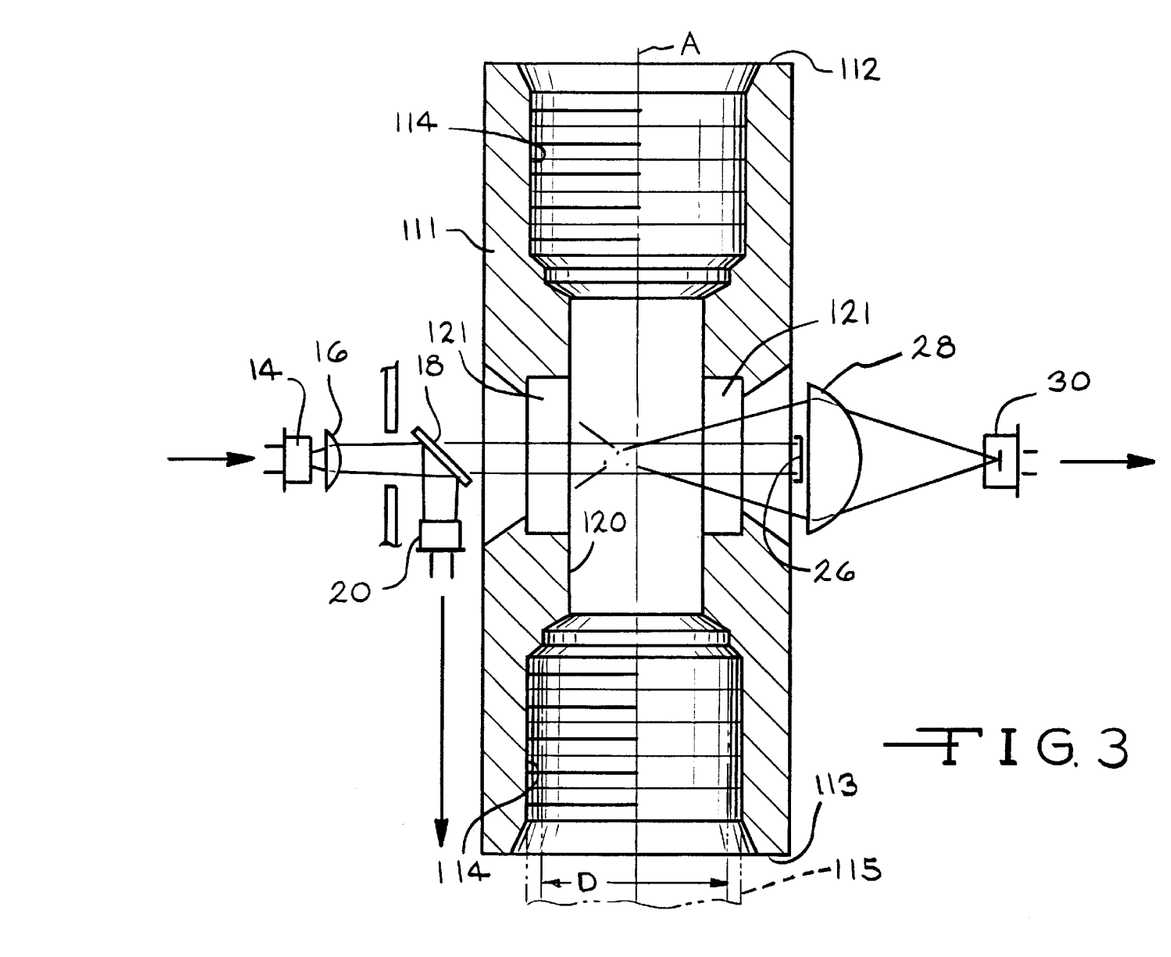
FIG. 3 is an enlarged fragmentary view of the optical portion of yet another embodiment.
Figure 4:
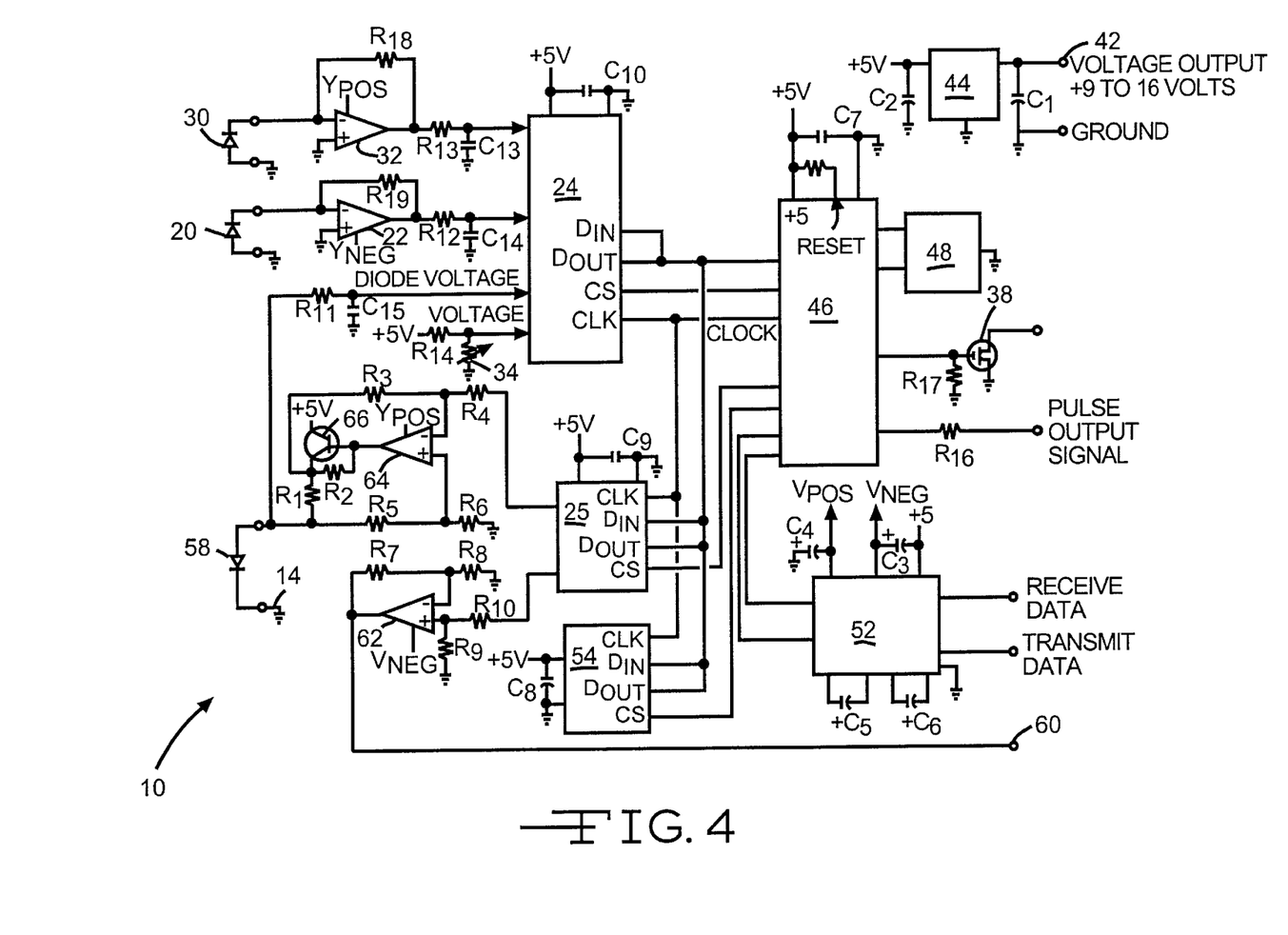
FIG. 4 is a schematic diagram of the circuitry for the digital electronics for the embodiment of FIG. 1.
Figure 5:
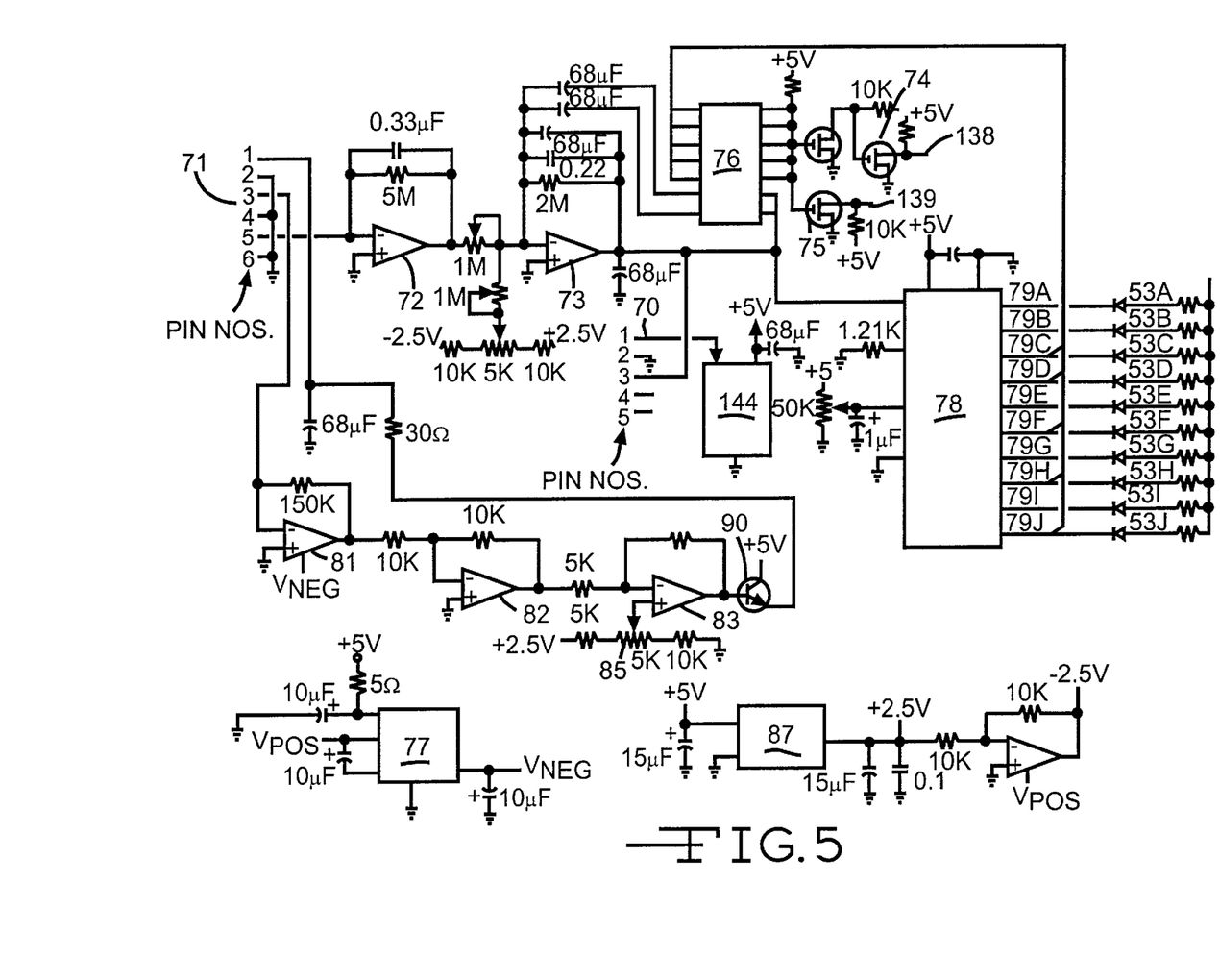
FIG. 5 is a schematic diagram of the circuitry for the analog electronics for the embodiment of FIG. 2.

The opto-electronic block diagram and schematic diagram with the analog circuit is shown in FIGS. 2 and 5 and with the digital circuit is shown in FIGS. 1 and 4. FIG. 3 shows another embodiment in which the portion of the tube being monitored has a smaller diameter than the other portions of the fluid flow line.

The embodiments are similar in that they use optical and electronic components to determine the quality or condition of a working fluid such as hydraulic oil in order to send out an alarm when the fluid is contaminated. The assembly diagrams show both configurations. They both use an infra-red light emitting diode source to send a strong light beam straight through the oil flowing through a fluid flow line to detect particles or contaminants in the oil.

If the main light beam (axial) hits any particles, bubbles or material, these elements scatter some of the light in many directions. An optical trap is aligned on the main axis of the light, on the opposite side of the oil chamber from the light source. The trap blocks the direct light coming from the source, and prevents it from hitting the optical photodiode detector. This axial beam "light trap" is critical to the sensitivity of this equipment.

Some of the scattered light redirected away from the main axis is collected by a lens and directed toward a light sensitive photodiode at the end of the path. This photodiode detects the scattered light signal and in turn gives an electrical signal that is used to send an output alarm about the condition of the oil if the contaminants in the oil increase beyond a predetermined level as measured by the amount of light reaching the detector photodiode. In the embodiment of FIGS. 2 and 5, the photodiode amplifier will send the signal directly to the signal processor which relays it to the alarm. In the embodiment of FIGS. 1 and 4, the photodiode amplifier will send the signal to an analog-to-digital converter which relays it to a microcomputer which relays it to the alarm.

Under one embodiment, the source of light is monitored by another photodiode and an electrical feedback control "loop" for the purpose of holding the light level (amplitude) constant. In this way, the reference light level passed through the oil chamber or "viewing volume", can be well controlled. However, it is also possible to utilize an infra-red light emitting diode which has a self-contained internal monitor for maintaining the light level constant thereby eliminating the need for an external monitoring photodiode or a beam splitter.

The differences in the digital and analog electrical circuit diagrams have to do mainly in the way the electrical signals are processed. The use of digital integrated circuits to process the signal voltages makes it easier to do temperature compensation of the electro-optic signal voltages than is possible with the analog circuits thereby improving the accuracy of the alarm signal over the high temperature operating conditions in which hydraulic equipment is used.

Referring to the drawings, FIGS. 1 and 4 show the fluid specification monitor (FSM) 10 with digital electronics with FIG. 1 showing a block diagram for such digital version. An oil chamber 11, such as a fluid flow line portion of a hydraulic return line directs the flow of hydraulic fluid H. As shown in FIG. 1, the hydraulic fluid H has contaminants such as particles P. The fluid flow line functioning as the oil chamber 11 has positioned therein a pair of windows 12A and 12B to permit viewing through the oil chamber 11 and to permit the transmission through the oil chamber 11 and the hydraulic fluid H passing therethrough of a beam of infra-red light from an infra-red light emitting diode 14. Positioned between the infra-red light emitting diode 14 and the oil chamber 11 is a lens 16 and a beam splitter 18. A portion of the light passing through the beam splitter 18, preferably about 70%, passes through the closest window 12A thereto, through the hydraulic fluid H and exits from the opposing window 12B along a path which is generally perpendicular to the flow of hydraulic fluid H through the oil chamber 11. Preferably an opaque shield 17 having an aperture 17A is mounted on or adjacent to the surface of the window 12A facing the infra-red light emitting diode 14. The shield 17 limits the amount of undesirable reflected light which may enter the chamber 11 and is effective in preventing false readings erroneously indicating the presence of excessive particles. As an example, if the window 12A has a diameter of one-half inch, the size of the aperture 17A will be 0.30 inch in diameter. For some applications, it may be desirable to have a plurality of shields with their respective apertures aligned along the alignment path. The other portion of the light reflected off of the beam splitter 18 is directed first to a monitoring photodiode 20 and then as an electrical current to a photodiode amplifier 22 and from there as a voltage to an analog-to-digital converter 24.

A light trap or mask 26 is positioned to receive light from the infra-red light emitting diode 14 as it exits the window 12B on the opposite side of the oil chamber 11 from the infra-red light emitting diode 14. The infra-red light may have a peak wave length of 880 nanometers. However, this could vary and the light could be other than infra-red. The trap 26 is aligned with the infra-red light emitting diode 14, the lens 16 and the windows 12A and 12B and has a size which will trap and block the light coming directly along such alignment path but will permit scattered light to pass therearound. The light trap has a diameter of about 4 millimeter (mm) and preferably is no larger than 5 mm in diameter.

Spaced from the light trap 26 is a lens 28 which receives the scattered light and focuses it on a detector photodiode 30. Preferably, the lens has a diameter of about 21 mm with a possible range in the size of the diameter of 18 to 30 mm. Light from the detector photodiode 30 is transmitted to a photodiode amplifier 32 which transmits the scattered light voltage to the analog-to-digital converter 24.

A feature of the digital embodiment of FIGS. 1 and 4 which is not present in the analog embodiment of FIGS. 2 and 5 is the presence of a thermally responsive resistor 34 which transmits information regarding temperature of the electrical and optical components, such as the infra-red light emitting diode 14 and photodiodes 20 and 30, to the analog-to-digital converter 24 for forwarding to a microcomputer 46 which calculates and compensates for variations in temperature. The analog-to-digital converter 24 also transmits to the microcomputer 46 information regarding the scattered light voltage received from the photodiode amplifier 32 and information regarding the monitored voltage received from the photodiode amplifier 22. If the microcomputer 46 computations indicate a high signal level as a result of contaminants viewed in the oil chamber 11, it will alert an output alarm signal transistor 38.

With additional reference to FIG. 4 along with FIG. 1, a +12 volt DC input voltage 42 from the vehicle or mobile equipment electrical system to which the monitor is mounted, goes into integrated circuit voltage regulator 44. The voltage regulator 44 provides a regulated +5 volts for the circuitry of the FSM 10. The voltage regulator 44 may be a National Semiconductor LM2937-5.0 or equivalent. The microcomputer 46, which provides the digital control, computation and logic for the system, may be a Microchip PIC 16C622 8 bit microcomputer or equivalent. The microcomputer 46 has a 4 megahertz oscillator using an external resonator circuit 48. This can be a 4.0 megahertz Murata ceramic resonator or a quartz crystal and two 22 picofarad ceramic capacitors. The output alarm signal transistor 38 (a MOSFET device such as 2N7000) is controlled directly from an output line from the microcomputer 46.

A bidirectional serial data interface integrated circuit 52 is provided and functions as a charge pump to generate +9 & −8 volts supply for the photodiode amplifiers 22 and 32. One example of the integrated circuit 52 is Maxim MAX232A. The use of the bidirectional serial data interface integrated circuit 52 internal charge pump assists in extending the power supply regulator 44. The amplifiers 22 and 32 may each be part of a dual operational amplifier such as Linear Technology LT1413.

An electrically erasable memory 54 such as a Microchip 93C66 or equivalent provides memory for the microcomputer 46. The circuit also includes a dual digital-to-analog converter 25 such as a Linear Technology LTC1446. The microcomputer 46 sends two digital numbers to the dual digital-to-analog converter 25 which generates two separate analog voltages. One of these is needed as the control signal for a current driver 58 for the infra-red light emitting diode 14. The other voltage controls an output voltage buffer amplifier 62 which provides an output voltage signal 60. Another amplifier 64 functions as part of the constant current driver 58 for the infra-red light emitting diode 14. Amplifiers 62 and 64 may each be part of a dual operational amplifier such as Linear Technology LT1413. A transistor 66, driven by the amplifier 64, controls the high current output to the infra-red light emitting diode 14. The transistor 66 is a 2N5582 or equivalent.

The photodiode 30 for scattered light detection and the monitored light photodiode 20 from the beam splitter 18 are connected to amplifiers 32 and 22, respectively. These amplifiers 32 and 22 convert the photodiode currents into voltage signals which, along with several other voltage signals, are measured by the analog-to-digital converter 24 that converts multiple channels of input voltages to an output digital number, one channel at a time, and then transmits such output digital number to the microcomputer 46.

This system operates as follows: The microcomputer 46 takes a fixed value from memory microchip 54 and sends it to the dual digital-to-analog converter 25 where it is converted to a voltage output to the amplifier 64 and the output voltage buffer amplifier 62. The output current drives the infra-red light emitting diode 14 to generate the light source. The monitoring photodiode 20 measures this light and is read by the analog-to-digital converter 24. The microcomputer 46 compares the reading and controls the infra-red light emitting diode 14 current and light level. Scattered light detected by the photodiode 30 is read the same way by the analog-to-digital converter 24 and the microcomputer 46. A high signal level from the detector photodiode 30 indicates excessive contamination and results in an output alarm being sent from the microcomputer 46 to the alarm output signal 38. Two other voltages are read by the analog-to-digital converter 24 for temperature compensation. One is the voltage directly across the infra-red light emitting diode 14, which is related to the internal diode temperature. The other one is from a thermistor 34, a thermally responsive resistor, whose voltage and temperature can be read by the analog-to-digital converter 24 and the microcomputer 46. Temperature compensation is done by calculation inside the microcomputer 46 using the data read by the circuit and adjustments are made electronically.

Referring to FIGS. 2 and 5, there is shown a fluid specification monitor (FSM) 50 with analog electronics. In FIG. 2 there is shown a block diagram for the analog version of the FSM 50. An oil chamber 11, such as a fluid flow line portion of a hydraulic return line directs the flow of hydraulic fluid H. As shown in FIG. 2, the hydraulic fluid H has contaminants such as particles P. The fluid flow line functioning as the oil chamber 11 has positioned therein a pair of windows 12A and 12B to permit viewing through the oil chamber 11 and to permit the transmission through the oil chamber 11 and the hydraulic fluid H passing therethrough of a beam of infra-red light from an infra-red light emitting diode 14. Positioned between the infra-red light emitting diode 14 and the oil chamber 11 is a lens 16 and a beam splitter 18. A portion of the light passing through the beam splitter passes through the closest window 12A thereto, through the hydraulic fluid H and exits from the opposing window 12B along a path which is generally perpendicular to the flow of hydraulic fluid H through the oil chamber 11. The other portion of the light exiting the beam splitter 18 is directed first to a monitoring photodiode 20 and then to a photodiode amplifier 83 and from there to a light source level control 84 which functions to insure that the amount of light being emitted from the infra-red light emitting diode 14 is constant.

A light trap or mask 26 is positioned to receive light from the infra-red light emitting diode 14 as it exits the window 12B on the opposite side of the oil chamber 11 from the infra-red light emitting diode 14. The trap 26 is aligned with the infra-red light emitting diode 14, the lens 16, the beam splitter 18 and the windows 12A and 12B and has a size which will trap and block the light coming directly along such alignment path but will permit scattered light to pass therearound.

Spaced from the light trap 26 is a lens 28 which receives the scattered light and focuses it on a detector photodiode 30. The sizes of the trap 26 and lens 28 are similar to those of the embodiment of FIGS. 1 and 4. Light from the detector photodiode 30 is transmitted to a photodiode amplifier 72. The photodiode amplifier 72 transmits the scattered light voltage to a signal processor 51. If the scattered light voltage reaches a level indicating excessive contamination of the hydraulic fluid H, the signal processor 51 will cause the alarm signal 53 to be activated.

With specific reference to FIG. 5, an integrated circuit (IC) voltage regulator 144 takes direct current (DC) input voltage of 12 volts and provides a regulated +5 volt output for the electronic circuitry. The voltage regulator 144 could be an IC device such as Power Trends 78SR105HC. The input voltage comes in through connector 70 on pin #1, with pin #2 serving as the ground return. The DC voltage/power supply components are shown on the schematic of FIG. 5 but not on the block diagram of FIG. 2.

An output driver transistor 90 delivers current to the infra-red light emitting diode 14 through pin #1 of connector 71 to which the infra-red light emitting diode 14 is connected.

Alarm output signals 138 and 139 are connected through pins #4 and #5 of the connector 70 and come from transistor switches 74 and 75. These transistor switches 74 and 75 are equivalent to BUZ11 MOSFET types. The signals for the transistor switches 74 and 75 are received through junction block 76 which in turn receives the signals from the outputs of a semiconductor driver array 78 that switches on a sequence of ten output lines 79A–79J when the input voltage increases. This semiconductor driver array 78 may be National Semiconductor LM3914. These 10 output lines 79A–79J activate a sequence of 10 output alarm indicators consisting of linear array of visible colored light emitting diodes, 53A through 53J. The first four indicators or light emitting diodes, 53A through 53D, are green indicating "Low/OKAY", the next three indicators, 53E through 53G are yellow indicating "Medium/Caution", and the last three indicators, 53H through 53J are red indicating "High/Alarm".

The signal input voltage into the semiconductor switch 78 that causes the output indicators to light comes from the two stage amplifier noise filter/integrator circuit. The first stage is the photodiode amplifier 72, which generates an output voltage signal from an input current from the scattered light detector photodiode 30 which is connected electrically through connector 71, pin 5 and to ground on pin 6. The second stage is a signal integrator and noise filter amplifier 73 giving a slow output signal response from a rapidly changing input. Both amplifiers 72 and 73, can be National Semiconductor type LF347, for example. These IC amplifiers are powered by DC voltages from charge pump 77 which generates +10 and –10 volts from the +5 volt regulated supply. The charge pump 77 may be a Linear Technology Part LT1054, for example. Also, a voltage reference device 87 provides a precision reference voltage of +2.5 volts for the circuit and is a Maxim type MAX873.

The light source feedback control loop begins at pin #3 of the connector 71. The monitoring photodiode 20 sends an input signal through pin #3 of connector 71 to an amplifier 81. The amplifier 81 sends a DC voltage to another amplifier 82 which changes the polarity of the input signal from negative to positive. A third amplifier 83 provides voltage gain for the light monitor signal sent by the monitoring photodiode 20. All three amplifiers 81, 82 and 83 are of a type such as National Semiconductor LF347. The third amplifier 83 also compares the signal voltage to a reference voltage input from an adjustable resistor 85, and reverses the output voltage from positive to negative. Resistor 85 setting creates the reference voltage of around +2.5 volts for the light source level.

In the operation of the control loop, a lower level of light emitted, as detected by the monitoring diode 20, results in lower output voltage from the first and second amplifiers 81 and 82. At the third amplifier 83, the lower input level is compared to the constant reference level, and detects a drop in voltage. The output then increases substantially due to the gain of the amplifier. This increasing output voltage is connected directly into the output driver transistor 90 input. The resulting increased drive current from the output driver transistor 90 goes to the infra-red light emitting diode 14 and corrects for the low light level detected by the monitor, thus completing the operation of the control loop. As previously mentioned, if the scattered light reaching the detector photodiode 30 from the lens 28 is reduced such that the amount of voltage transmitted from the photodiode amplifier 72 to the signal processor 51 indicates excessive contamination of the hydraulic fluid H (i.e. excessive particles P), the signal processor will cause the alarm output 53 to be activated.

Referring to FIG. 3, the fluid specification monitoring system is shown in use with a fluid flow line section 111. In this embodiment, the fluid flow line section 111 extends along an axis A from a first end 112 to a second end 113 and has inwardly facing threads 114 adjacent each of said first end 112 and said second end 113. As shown in phantom lines, a tubular section 115 having an internal diameter D is engaged to the threads 114 at the second end 113. Another tubular section (not shown) is engaged to the threads 114 at the first end 112.

The fluid flow line section 111 has a constricted area 120 having a diameter which is smaller than the internal diameter D of the tubular sections 115. A pair of windows 121 are mounted in the constricted area 120 on opposite sides of the axis A and aligned such that the beam of infra-red light emitted from the infra-red light emitting diode 14 passes through each of the windows 121.

The embodiments of FIGS. 1, 4 and 2, 5 both utilize a beam splitter 18 and a monitoring photodiode 20 for insuring against faulty readings activating the alarm signal due to variations in the amount of light emitted by the infra-red light emitting diode 14. Preferably by maintaining the intensity of the light at a constant level, it is also possible to utilize the broad concept of the present invention without using a beam splitter 18.

Under one embodiment, this is accomplished by utilizing a self-monitoring light emitting diode, for example, one manufactured by Integrated Photomatrix Inc., Hillard, Ohio under its Part No. IPL 10630.

Figure 6:
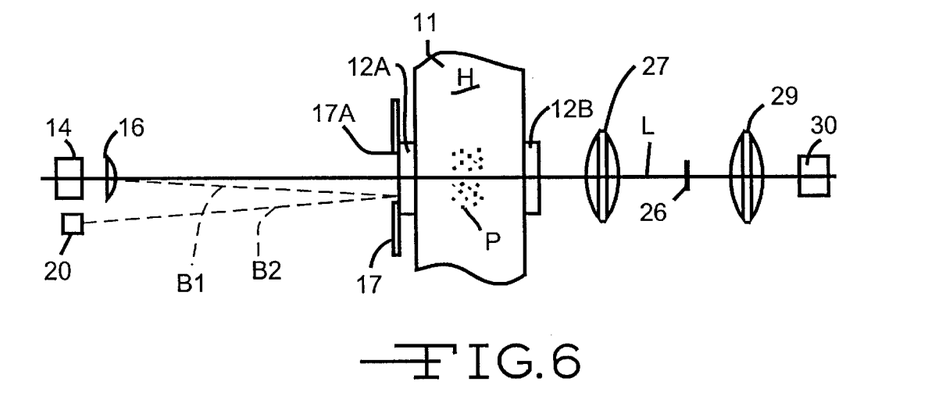
FIG. 6 is an optical diagram showing a further embodiment.

Under another embodiment, as shown in FIG. 6, the elimination of the beam splitter 18 is accomplished by positioning the monitoring photodiode 20 in a location where it can capture light from the infra-red light emitting diode 14 which is reflected off of the window 12A. This is shown in FIG. 6 which shows the monitoring photodiode 20 positioned adjacent to the infra-red light emitting diode 14. As shown in dashed lines, the light from the infra-red light emitting diode 14 exiting the lens 16 includes a divergent beam portion B1 which, after striking the surface of the window 12A at an angle to the line of alignment L of the infra-red light emitting diode 14 and the light trap 26 is reflected back as a reflected beam portion B2 which is read by the monitoring photodiode 20.

FIG. 6 also shows a preferred system of lenses. As in the embodiment of FIG. 1, a lens 16 is positioned between the infra-red light emitting diode 14 and the window 12A, being much closer to the diode 14 than to the window 12A. The shield 17, having an aperture 17A, is mounted on or closely adjacent to the receiving surface of the window 12A in order to restrict to the greatest extent possible the light source entering the window 12A to that which is emitted by the infra-red light emitting diode 14. On the opposite side of the chamber 11, spaced from the window 12B, is a first double convex lens 27. A second double convex lens 29 is positioned between the first double convex lens 27 and the detector photodiode 30. The light trap 26 is positioned between the two double convex lenses 27 and 29 but much closer to the second double convex lens 29 or even in contact with the surface thereof.

The first double convex lens 27 receives light exiting the window 12B and focuses it onto the light trap 26 with any scattered light resulting from contamination by particles P reaching the second double convex lens 29 which focuses such scattered light to the detector photodiode 30.

Figure 7:
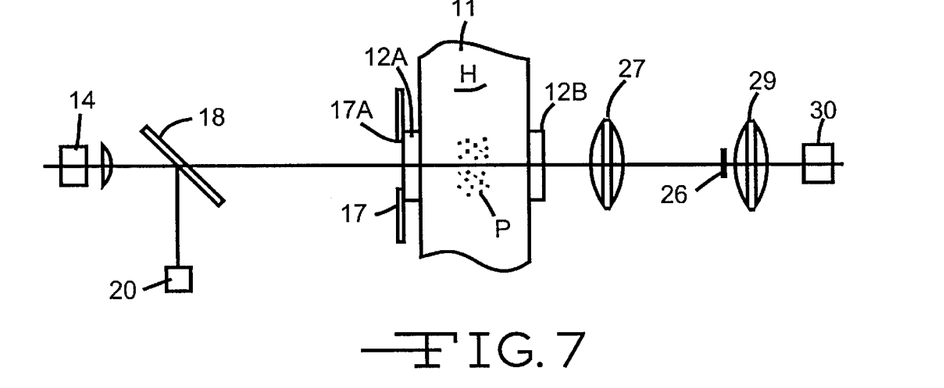
FIG. 7 is an optical diagram showing yet another embodiment.

FIG. 7 shows a further preferred embodiment which utilizes double convex lenses 27 and 29 as in the embodiment of FIG. 6 but which utilizes a beam splitter 18 for directing the split beam to the monitoring photodiode 20.

The size and cross-sectional size and configuration of that portion of the monitoring device containing the windows and the hydraulic fluid to be monitored (i.e. the view chamber) may be varied depending upon the flow rate, pipe diameter and optic performance. For example, it is within contemplation of the present invention that the viewing chamber containing the windows have a rectangular as well as circular or other cross-sectional configuration. Additionally, for some applications it may be desirable that the cross-sectional size of such viewing chamber be larger that the size of the pipes directing the flow of liquid therethrough.

In addition to the embodiments discussed above, it will be clear to persons skilled in the art that numerous modifications and changes can be made to the above invention without departing from its intended spirit and scope.

I claim:

1. Apparatus for detecting particulate debris in hydraulic fluid flowing in a fluid flow system of operating equipment comprising
   (a) a fluid flow line for directing the flow of hydraulic fluid, said fluid flow line having a section permitting the transmission of light therethrough;
   (b) a source of light directed toward said section for transmission through said section and through hydraulic fluid or oil flowing through said section;
   (c) a light detector positioned to receive light from said light source passing through said flow line section and hydraulic fluid flowing therethrough while said equipment is operating;
   (d) a trap located outside of said flow line section positioned between said flow line section and said detector, said trap having a size preventing the direct passage of said light to said detector while permitting scattered portions of said light to reach said detector; and
   (e) an alarm responsive to a decrease in the amount of light reaching said detector.

2. The apparatus of claim 1 wherein said source of light emits infra-red light.

3. The apparatus of claim 2 wherein said trap has a diameter in the range of 4 mm to 5 mm.

4. The apparatus of claim 2 further including a shield positioned between said source of light and said fluid flow line section, said shield having an aperture sized to substantially restrict the light reaching said flow line section to that emitted by said source of light while minimizing the amount of reflected light reaching said flow line section.

5. The apparatus of claim 1 further including a lens between said trap and said detector, said lens receiving said scattered light portions and causing said scattered light portions to be concentrated on said detector.

6. The apparatus of claim 5 wherein said trap has a diameter in the range of 4 mm to 5 mm and said lens has a diameter of at least 18 mm.

7. The apparatus of claim 5 further including a second lens positioned between said flow line section and said trap.

8. The apparatus of claim 1 further including a light monitor and a beam splitter for receiving said light from said light source and directing (i) a first portion of said light to pass through said flow line section and fluid flowing therethrough and (ii) a second portion of said light to said monitor.

9. The apparatus of claim 8 wherein said alarm includes a digital control microcomputer and wherein the amount of decrease in said light required to activate said alarm is related to the amount of light reaching said monitor.

10. The apparatus of claim 1 further including a light monitor positioned to receive a portion of light emitted by said source of light and reflected from said flow line section.

11. The apparatus of claim 1 further including a temperature sensing device for determining the temperature of fluid flowing through said fluid flow line, said temperature sensing device causing a variation in the magnitude of decrease in light required to activate said alarm.

12. The apparatus of claim 1 wherein said fluid flow system includes tubular portions engaged to said flow line section, said flow line section having a smaller cross sectional size than said tubular portions.

13. Apparatus for detecting particulate debris in a fluid flowing through a fluid flow system of operating equipment comprising
    (a) a fluid flow line extending along an axis;
    (b) first and second window portions in said fluid flow line in opposite sides of said axis, said first and second window portions permitting the transmission of light therethrough;
    (c) a source of infra-red light directing light toward said first window portion said light having the capability of passing through fluid as it flows through said fluid flow line during operation of said equipment;
    (d) a light detector positioned to receive light from said light source passing through said flow line, said flowing fluid and out of said second window portion;
    (e) a trap located outside of said flow line and positioned between said second window portion said detector, said trap having a size preventing the direct passage of said light to said detector while permitting scattered portions of said light to reach said detector; and
    (f) an alarm system responsive to a decrease in the amount of light reaching said detector, said alarm system including a digital control microcomputer.

14. The apparatus of claim 13 further including a lens between said trap and said detector, said lens receiving said scattered light portions and causing said scattered light portions to be concentrated on said detector.

15. The apparatus of claim 14 wherein said trap has a diameter in the range of 4 mm to 5 mm and said lens has a diameter of at least 18 mm.

16. The apparatus of claim 14 further including a second lens positioned between said second window portion and said trap.

17. The apparatus of claim 13 further including a shield positioned between said source of light and said first window portion, said shield having an aperture sized to substantially restrict the light reaching said first window portion to that emitted by said source of infra-red light while minimizing the amount of reflected light reaching said flow line section.

18. The apparatus of claim 13 further including a light monitor and a beam splitter for receiving said light from said light source and directing (i) a first portion of said light to pass through said flow line and fluid flowing therethrough and (ii) a second portion of said light to said monitor.

19. The apparatus of claim 18 wherein the amount of decrease in said light required to activate said alarm is related to the amount of light reaching said monitor.

20. The apparatus of claim 13 further including a light monitor positioned to receive a portion of light emitted by said source of infra-red light and reflected from said first window portion.

21. The apparatus of claim 20 wherein the amount of decrease in said light required to activate said alarm is related to the amount of light reaching said monitor.

22. The apparatus of claim 13 further including a temperature sensing device for determining the temperature of fluid flowing through said fluid flow line, said temperature sensing device causing a variation in the magnitude of decrease in light required to activate said alarm.

23. The apparatus of claim 13 wherein said fluid flow system includes tubular portions engaged to said flow line section, said flow line section having a smaller cross sectional size than said tubular portions.

24. A method for detecting particulate debris in hydraulic fluid flowing in a fluid flow line of equipment comprising the steps of:
    (a) providing a flow line section having an axis along which fluid flows, said section permitting light to pass therethrough at substantially right angles to said axis;
    (b) while said equipment is operating, causing infra-red light to pass through (i) said section and (ii) fluid flowing therethrough;
    (c) providing a light detector; and
    (d) positioning a trap outside of said flow line section to block direct light exiting said fluid flow line section while permitting scattered light to reach said light detector.

25. The method according to claim 24 further including the step of activating an alarm upon a reduction in the amount of light reaching said light detector through use of a digitally controlled microcomputer.

26. The method according to claim 24 further including the step of passing said scattered light through a lens prior to its reaching said light detector.

27. The method according to claim 24 further including the steps of causing a portion of said infra-red light to be directed to a monitor without passing through said flow line section and fluid and activating an alarm upon a variation in the relative amounts of infra-red light reaching said light detector and said monitor.

28. The method according to claim 27 further including the step of monitoring the temperature of fluid flowing through said fluid flow line section and coordinating variations in said temperature with the magnitude in the difference between (i) the amount of light reaching said monitor and (ii) the amount of light reaching said light detector required to activate said alarm.

29. The method according to claim 24 further including the step of causing said fluid flow line section to have the same cross sectional flow area as portions of said fluid flow line adjacent thereto.

30. The method according to claim 24 further including the step of causing said fluid flow line section to have a smaller cross sectional flow area than portions of said fluid flow line adjacent thereto.

31. The method of claim 24 further including the step of positioning a shield between said infra-red light and said flow line section, said shield having an aperture sized to substantially restrict the light reaching said flow line section to that emitted by said source of infra-red light while minimizing the amount of reflected light reaching said flow line section.

\* \* \* \* \*